(12) United States Patent
Nishibe et al.

(10) Patent No.: US 8,182,824 B2
(45) Date of Patent: May 22, 2012

(54) CICLESONIDE-CONTAINING STERILE AQUEOUS SUSPENSION

(75) Inventors: Yoshihisa Nishibe, Yamaguchi (JP); Atsuhiro Nagano, Tokyo (JP); Kazuya Takanashi, Tokyo (JP); Yasuhide Uejima, Tokyo (JP)

(73) Assignee: NYCOMED GmbH, Constance (DE)

( * ) Notice: Subject to any disclaimer, the term of this patent is extended or adjusted under 35 U.S.C. 154(b) by 644 days.

(21) Appl. No.: 10/519,484

(22) PCT Filed: Jul. 2, 2003

(86) PCT No.: PCT/JP03/08410
§ 371 (c)(1),
(2), (4) Date: Jul. 21, 2005

(87) PCT Pub. No.: WO2004/004739
PCT Pub. Date: Jan. 15, 2004

(65) Prior Publication Data
US 2006/0166953 A1 Jul. 27, 2006

(30) Foreign Application Priority Data
Jul. 2, 2002 (JP) .................................. 2002-193399

(51) Int. Cl.
*A61K 9/00* (2006.01)
*A61K 31/58* (2006.01)
*A61L 2/08* (2006.01)
(52) U.S. Cl. ........................... 424/400; 422/26; 514/174
(58) Field of Classification Search .................. 424/523; 514/174, 179; 540/84, 85
See application file for complete search history.

(56) References Cited

U.S. PATENT DOCUMENTS

| 3,288,679 A | 11/1966 | Fried et al. |
| 3,962,430 A | 6/1976 | O'Neill |
| 2002/0065256 A1* | 5/2002 | Karlsson et al. ............... 514/174 |

FOREIGN PATENT DOCUMENTS

| EP | 0 233 849 B1 | 6/1991 |
| JP | 62-192322 | 8/1987 |
| JP | 2001-048807 | * 8/1987 |
| JP | 2001-48807 | 2/2001 |
| JP | 2004-035441 | 2/2004 |
| WO | 99/25359 A1 | 5/1999 |
| WO | 99/32156 A1 | 7/1999 |
| WO | 01/28562 A1 | 4/2001 |
| WO | 01/28563 A1 | 4/2001 |
| WO | WO 01/28563 A * | 4/2001 |
| WO | 02/41925 A1 | 5/2002 |

OTHER PUBLICATIONS

Material Safety Data Sheet for HPMC 2019 (aka Metolose 60SH)—provided by Shin-Etsu Co.*
http://en.wikipedia.org/wiki/Difluprednate.*
JP 2001-048807 Machine Translation.*
U.S. Patent Documents—None.*
Non-Patent Documents—None.*
Illum, L., et al., "Surface area stability of micronized steroids sterilized by irradiation", *Arch. Pharm. Chemi Sci. Ed.*, vol. 2, pp. 167-174, (1974).
Zhang, et al., "Effect of drug particle size on content uniformity of low-dose solid dosage forms", International Journal of Pharmaceutics, vol. 154, pp. 179-183, (1997), Elsevier Science Ireland Ltd.

* cited by examiner

*Primary Examiner* — Robert A Wax
*Assistant Examiner* — Jeffrey T Palenik
(74) *Attorney, Agent, or Firm* — The Nath Law Group; Sheldon M. McGee

(57) ABSTRACT

The present invention provides a ciclesonide-containing sterile aqueous suspension sterilized by autoclaving, wherein the concentration of ciclesonide after autoclaving is 95% or more compared to that before autoclaving.

1 Claim, 2 Drawing Sheets ature. But the third method, the autoclaving, is the most useful sterilizing method as long as the drug is stable enough not to be degraded under such high temperature.

CICLESONIDE-CONTAINING STERILE AQUEOUS SUSPENSION

FIELD OF INVENTION

The present invention relates to a ciclesonide-containing sterile aqueous suspension sterilized by autoclaving. Besides, the present invention relates to a method of manufacturing a ciclesonide-containing sterile aqueous suspension comprising the step of sterilization by autoclaving a ciclesonide-containing aqueous suspension.

BACKGROUND ART

The pharmaceutical composition of the present invention is a suspension. The suspension can be obtained by suspending a water-insoluble drug(active ingredient) in aqueous medium uniformly. The suspension can be administered in a specific dosage form. Not only a stability of pharmaceutical compositions during storage, but also a high retentivity of drug in the administration site such as nasal cavity can be obtainable by using suspending agents with thixotropic property.

Therefore, the aqueous suspension has been recognized as a useful dosage form and many suspension products have been available on the market.

It is potentially easy for microorganism such as bacteria to proliferate in the aqueous suspension due to its high moisture environment.

Therefore, preservatives are necessary to be added in such aqueous suspension for supplying the market. Generally, as such preservatives, benzalkonium chloride, benzethonium chloride, phenylethyl alcohol or paraoxybenzoic acid esters are used. However, these preservatives are undesirable for use because the damages on mucous membrane etc. as reported in not a few literatures.

For avoiding proliferation of microorganism without preservatives in aqueous formulation, several methods mentioned-below are actually used in general.

The first method is to prepare an aqueous formulation from sterilized ingredients under aseptic condition. The second method is to prepare an aqueous formulation from non-sterilized ingredients, and then, the obtained aqueous formulation is sterilized before or after filling in bottles. In the case of suspension, with respect to the first method, Karlsson et al. disclosed a steroid-containing composition sterilized by dry heat sterilization (WO99/25359). To provide the sterile aqueous suspension, however, it is needed that the suspension has to be prepared under aseptic condition throughout the manufacturing process with sterilized ingredients including steroid, indicating that large and special manufacturing plant is necessary.

On the other hand, as the second method that is simpler than the first one from the viewpoint of equipments, some specific methods have been suggested as follows.

Firstly, filtration. However this method of sterilization is not applicable to suspension in general, because the suspension contains insoluble particles.

Secondly, radiation sterilization. For example, Illum et al. recommended a sterilization process for steroid-containing aqueous suspension by beta ray or gamma ray irradiation (Arch. Pharm. Chemi. Sci., Ed. 2, 1974, pp. 167-174). However, it is known that many compounds including steroids and other possible ingredients are degraded by beta ray or gamma ray irradiation and then it is difficult to guarantee the security of the degradation products. Therefore, the sterilization methods recommended by Illum et al. are not unlikely applicable to pharmaceutical compositions in actuality.

Thirdly, autoclaving. The autoclaving is one of very common sterilization processes for sterilizing of pharmaceutical compositions. Since the autoclaving is done by heating at 121 degrees C., the method cannot be adopted for unstable drugs in the presence of water at such high temperature. But the third method, the autoclaving, is the most useful sterilizing method as long as the drug is stable enough not to be degraded under such high temperature.

However, there are still two problems to be solved as indicated below.

First, ciclesonide did not seem to be stable chemically at such high temperature, because ciclesonide has an acetal structure in its 16 and 17 positions.

Secondly, it is known that a drug content uniformity (The term "drug content uniformity" means that the drug concentrations sampled from any portions(ex. upper portion, middle portion or lower portion) of the suspension are almost same.) of aqueous suspension containing a water-insoluble drug tends to be depressed by autoclaving, even if the drug is chemically stable. Such a phenomenon, the depression of the content uniformity, is explained that some particles of water-insoluble drug that are once dissolved or partly dissolved to smaller particles under such high temperature appeared again as various size of particles during subsequent cooling, leading to wider range of particle size distribution in suspension.

O'Neill et al. suggested a method by adding saturated concentration of sodium chloride for avoiding depression of the content uniformity of water insoluble drug (U.S. Pat. No. 3,962,430). But, in case adding the saturated concentration of sodium chloride solution, osmotic pressure of the aqueous suspension becomes extremely high. Or the suspension becomes unstable, because the important factor to maintain the physical stability of suspension is matrix network resulted mainly from hydrogen bond that is easily destroyed by high ionic strength. The patent application by Nagano et al. (WO 01/28562) described the aqueous pharmaceutical composition having less than 290 mOsm osmotic pressure comprising ciclesonide and hydroxypropylmethylcellulose("HPMC" hereinafter). In addition, the patent application by Nagano et al. (WO 01/28563) described the aqueous pharmaceutical composition comprising ciclesonide and HPMC.

However, Nagano et al. did not mention or suggest sterilizing the composition by autoclaving. Furthermore, Nagano et al. disclosed in these specifications that preservatives might be added to the pharmaceutical composition.

Therefore, there is no motivation concerning the composition without preservatives in both specifications.

The object of the present invention is to provide a ciclesonide-containing sterile aqueous suspension without preservatives.

Further, the other object of the present invention is to provide such a ciclesonide-containing sterile aqueous suspension that can maintain content uniformity of ciclesonide.

The above objects of the present invention have been achieved by discovering that ciclesonide content in the ciclesonide containing aqueous suspension is not depressed by autoclaving, namely, ciclesonide is not degraded by autoclaving in the aqueous suspension.

Further, the above objects of the present invention have been achieved by discovering that the uniformity of ciclesonide content can be maintained when hydroxypropylmethylcellulose is coexisted, even after sterilization by autoclaving.

BRIEF DESCRIPTION OF THE DRAWING

● of 1: Ex. 1 lower, ▲ of 2: Ex. 1 middle, X of 3: Ex. 1 upper
● of 4: C.Ex. 3 lower, ▲ of 5: C.Ex. 3 middle, X of 6: C.Ex. 3 upper
● of 7: C.Ex. 4 lower, ▲ of 8: C.Ex. 4 middle, X of 9: C.Ex. 4 upper
● of 10: C.Ex. 5 lower, ▲ of 11: C.Ex. 5 middle, X of 12: C.Ex. 5 upper
● of 13: C.Ex. 6 lower, ▲ of 14: C.Ex. 6 middle, x of 15: C.Ex. 6 upper
● of 16: C.Ex. 7 lower, ▲ of 17: C.Ex. 7 middle, X of 18: C.Ex. 7 upper

DISCLOSURE OF THE INVENTION

Figure 1:
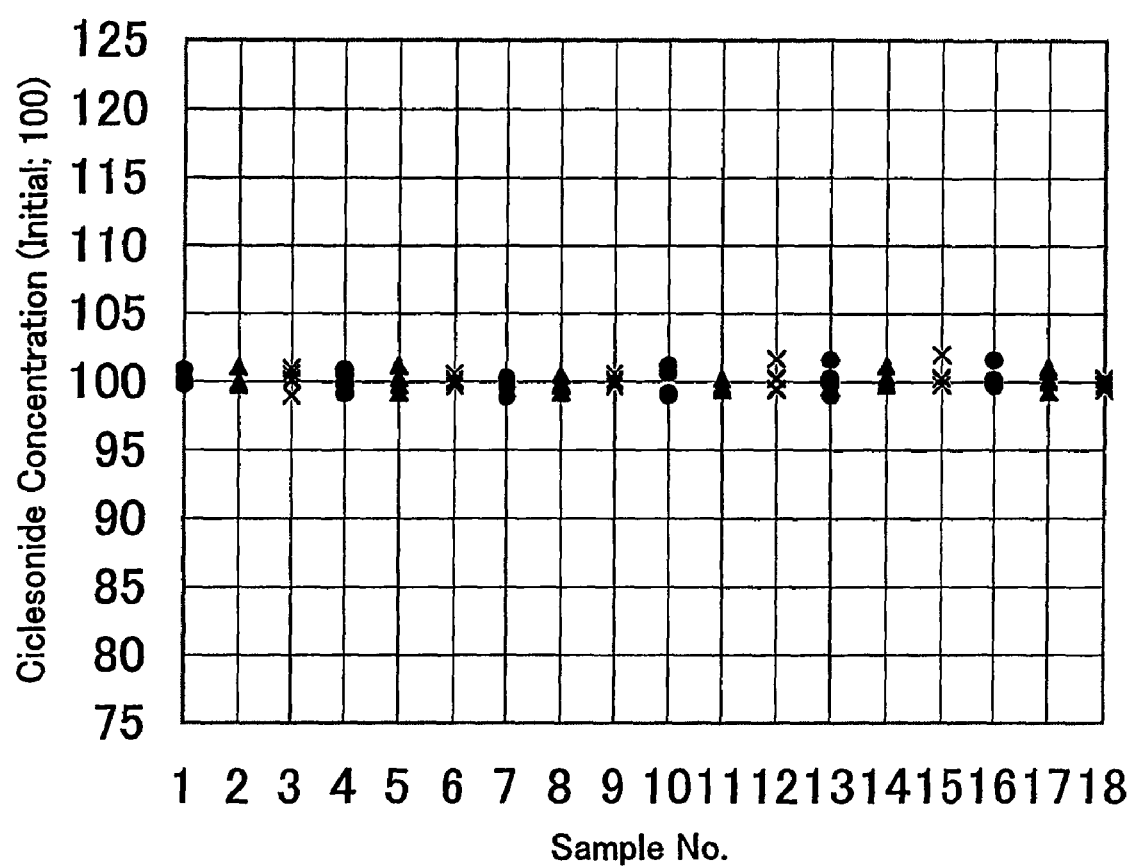
FIG. 1 shows ciclesonide concentration before autoclave, and corresponds to Table 2. Legends in FIG. 1 mean as follows.

The present invention provides a ciclesonide-containing sterile aqueous suspension sterilized by autoclaving, wherein the concentration of ciclesonide after autoclaving is 95% or more comparing to that before autoclaving.

Also the present invention provides the ciclesonide-containing sterile aqueous suspension sterilized by autoclaving, wherein the suspension contains hydroxypropylmethylcellulose.

Further the present invention provides a method of manufacturing a ciclesonide-containing sterile aqueous suspension comprising the step of sterilization by autoclaving a ciclesonide-containing aqueous suspension.

EMBODIMENT FOR CARRYING OUT THE INVENTION

Ciclesonide used in the present invention is a kind of steroids, and represented by the chemical name of $(11\beta,16\alpha)$-16,17-[cyclohexylmethylenebis(oxy)]-11-hydroxy-21-(2-methyl-1-oxopropoxy)pregna-1,4,-diene-3,20-dione.

The concentration of ciclesonide after autoclaving is 95% or more comparing to that before autoclaving in the present invention. Further, according to the condition of the autoclaving, the concentration of ciclesonide after autoclaving may be 98% or more comparing to that before autoclaving.

Chemically unstable substances are usually degraded by autoclaving or even heating. For example, budesonide (chemical name: $16\alpha,17$-[(1RS)-butylidene-bis(oxy)]-$11\beta$,21-dihydroxypregna-1,4-diene-3,20-dione), a kind of steroids, same class of drugs as ciclesonide, is degraded by autoclaving procedure.

But surprisingly, ciclesonide of the present invention is not degraded by autoclaving procedure though ciclesonide has an acetal structure in its 16,17 position.

The concentration of ciclesonide in the present invention is not specified. Preferably, the concentration of the ciclesonide is from 0.01% w/w to 10% w/w, more preferably, from 0.01% w/w to 3% w/w, relative to the total amount of the suspension.

HPMC is a kind of wetting agents. HPMC is heteropolymer composed of a mixture of methyl and hydroxypropyl ether of cellulose derivative. HPMC is used for an additive of pharmaceutical composition in general. HPMC has several grades classified depending on content of methoxyl group and hydroxypropoxyl group. Although any grade can be used for the suspension of the present invention, specific examples are hydroxypropylmethylcellulose 2208, hydroxypropylmethylcellulose 2906, or hydroxypropylmethylcellulose 2910. These grades of HPMC are available as Metolose 90SH, Metolose 65SH or Metolose 60SH (by Shin-Etsu Chemical CO.), respectively. Preferably, hydroxypropylmethylcellulose 2910, i.e. Metolose 60SH, is suitable.

Although said HPMC may be present at any concentration, its concentration is preferably from 0.01% w/w to 5% w/w, more preferably from 0.05% w/w to 1% w/w, relative to the total amount of the suspension.

HPMC is effective for overcoming the depression of ciclesonide content uniformity by autoclaving in the present invention with no need to add salt such as sodium chloride. As mentioned below, HPMC is superior in overcoming the depression of ciclesonide content uniformity to general surfactants used as wetting agents.

Although hydroxypropylcellulose (HPC) or carmellose sodium(CMCNa) can be illustrated as cellulose ethers, they are not suitable due to the followings. HPC forms gel during the autoclaving process, resulting in poor uniformity of drug content besides undesirable look by appearance.

Suspending agents can be added to the present suspension, if desired. Any suspending agents can be applied in the present invention. Examples of suspending agents include polyvinyl alcohol, povidone, cellulose, carbomer, poloxamer, carmellose sodium and xanthangum. Complexes of water insoluble substances and dispersants may be used as the suspending agent. Example of the water-insoluble substance includes microcrystalline cellulose, examples of the dispersants include carmellose sodium and xanthangum. Preferably, complex of microcrystalline cellulose and carmellose sodium is suitable for the present invention. The complex called microcrystalline cellulose-carmellose sodium in general, is available as Avicel™ RC-591NF from Asahi Kasei Co., Ltd. The concentration of suspending agent of the present invention is preferably from 0.1% w/w to 10% w/w, more preferably 0.5% w/w to 5% w/w, relative to the total amount of the suspension. Any method for dispersing ciclesonide in an aqueous medium optionally including HPMC and suspending agent may be used for the production of the ciclesonide-containing aqueous suspension in the present invention, a specific example of which is a method that uses commercially available equipment such as a mixer and an emulsifier. Preferably, a vacuum emulsifier is suitable for evacuating bubbles growing in the dispersing process. It is preferable for the condition to be set that leads to both good drug content uniformity and maximum thixotropic property.

The autoclaving of the present invention is a method of sterilizing in autoclaving equipment by steam with high pressure and temperature. A proper condition should be set depending on the equipment used or the scale of bulk suspension to be dealt with. Generally, the autoclaving is carried out at 115 degrees C. for 30 minutes, at 121 degrees C. for 20 minutes or at 126 degrees C. for 15 minutes.

The suspension can be autoclaved consecutively in the same container used for the dispersion, or after filling in another container. In the case of former method, with the equipment having special apparatus, both dispersion and sterilization can be done.

After sterilization process by autoclaving, the ciclesonide-containing sterile aqueous suspension of the present invention should be packaged in a container-closure system that has a structure avoiding contamination of microorganism such as bacteria. Several examples of such system are proposed. A filtering system equipped with the device for the avoidance of microorganism contamination accompanied with air flow after the actuation (spraying or dropping) is one example of such system. Another is an anti-microbial system such that the material to contact with the formulation is coated with silver. Or the combination of the above-mentioned systems is suitable. Preservative-free-system obtained from Pfeiffer is an example of the aforementioned system, but not limited to Pfeiffer's system.

The ciclesonide-containing sterile aqueous suspension of the present invention can be administered via any other routes than nasal route such as ophthalmic, transdermal or oral route. According to the present invention as described above, a ciclesonide-containing sterile aqueous suspension without preservatives is provided. In addition, according to the present invention as described above, a ciclesonide-containing sterile aqueous suspension is provided that has an excellent content uniformity of ciclesonide. Thus, the present invention has extremely high significance in terms of overcoming the possible side effects caused by preservatives.

EXAMPLES

The following provides an explanation of the present invention through its Examples.

Ciclesonide used in the present invention was obtained from Altana Pharma AG, the microcrystalline cellulose-carmellose sodium from Asahi Kasei Co., Ltd. (Avicel™ RC-A591NF), hydroxypropylmethylcellulose 2910 from Shin-Etsu Chemical Co., Ltd., (TC-5RW™), budesonide and beclomethasone dipropionate from Sigma-Aldrich Co. Desk Autoclave IST-150 from Chiyoda Manufacturing Co., Ltd. was used for autoclaving.

Example 1, Comparative Examples 1-2

Preparation of Ciclesonide-Containing Aqueous Pharmaceutical Suspension

White uniform aqueous pharmaceutical suspension containing the ingredients indicated below was prepared.

| Composition: | |
|---|---|
| Ciclesonide | 0.1% w/w |
| Microcrystalline Cellulose-Carmellose Sodium | 1.7% w/w |
| Hydroxypropylmethylcellulose 2910 | 0.1% w/w |
| Purified Water | 300 mL |

An aqueous suspension containing budesonide instead of ciclesonide of Example 1 was prepared as Comparative Example 1. An aqueous suspension containing beclomethasone dipropionate instead of ciclesonide of Example 1 was prepared as Comparative Example 2. Suspensions of Comparative Examples 1 and 2 were white and uniform.

Investigation 1
Comparison of Chemical Stability of Drug in the Aqueous Suspension Against Autoclaving
Procedure The suspension of Example 1 was put into a 500 mL glass container with a screw cap and sterilized by autoclaving at 121 degrees C. for 20 minutes. Subsequently, after mixing the suspension in the glass container, the ciclesonide concentration was quantified by HPLC.

The recovery rate of ciclesonide after the autoclaving was calculated by taking the ciclesonide concentration before the autoclaving to be 100%. The recovery rates of budesonide and beclomethasone dipropionate after the autoclaving were calculated by the same method.

Those rates are shown in Table 1.

TABLE 1

| Preparation | Recovery rate (%) |
|---|---|
| Example 1 | 100.1 |
| Comparative Example 1 | 26.3 |
| Comparative Example 2 | 78.1 |

Investigation 2
Comparison of Ciclesonide Concentration Uniformity of Aqueous Suspensions with Various Wetting Agents Before and after Autoclaving
Procedure Ciclesonide aqueous suspension containing wetting agents indicated below instead of hydroxypropylcellulose 2910 were prepared as Comparative Examples 3-7. Tween 80 used in the present invention was obtained from Nikko Chemicals Co., (Nikkol TO-10M), Tween 60 from Nikko Chemicals Co., Ltd. (Nikkol TS-10), Polyoxyethylene hydrogenated castor oil 60 from Nikko Chemicals Co., Ltd. (Nikkol HCO-60), hydroxypropylcellulose from Shin-Etsu Chemical Co., Ltd. (hydroxypropylcellulose) and carmellose sodium from Daiichi Kogyo Pharmaceutical Co., Ltd. (serogen).

| | |
|---|---|
| Comparative example 3: Tween 80 | 0.025% w/w |
| Comparative example 4: Tween 60 | 0.025% w/w |
| Comparative example 5: Polyoxyethylene Hydrogenated Castor Oil 60 | 0.2% w/w |
| Comparative example 6: Hydroxypropylcellulose(HPC) | 0.1% w/w |
| Comparative example 7: Carmellose Sodium | 0.15% w/w |

Each concentration of the wetting agent of Comparative Examples 3-7 was an optimum value as a wetting agent for suspension respectively. Therefore, by comparing with Example 2 and Comparative Examples 3-7, we can recognize differences between HPMC and other wetting agents(Tween 80, Tween 60, Polyoxyethylene Hydrogenated Castor Oil 60, HPC and Carmellose Sodium).

On 3-hour-leaving after the preparation of the above-mentioned suspension, dispersion states of solid particles in the suspension were observed. Furthermore about 2 g of the suspension was sampled from upper, middle and lower portions of the bulk suspension in the glass container, respectively, followed by the determination of ciclesonide concentration in each portion.

Appearances of the ciclesonide aqueous suspension and the uniformity of the ciclesonide concentration before autoclaving are shown in Table 2 and FIG. 1.

TABLE 2

| | | Ciclesonide concentration* (%) (versus theoretical value) | | |
|---|---|---|---|---|
| Preparation | Appearance | Upper portion of the bulk suspension (n = 5) | Middle portion of the bulk suspension (n = 5) | Lower portion of the bulk suspension (n = 5) |
| Example 2 | white and uniform suspension | 99.8, 100.9, 99.9 100.1, 100.1 | 99.9, 101.1, 99.8 99.8, 100.0 | 99.0, 100.2, 100.6 100.1, 101.0 |
| Comparative Example 3 | white and uniform suspension | 99.1, 99.9, 100.5 100.9, 99.8 | 100.3, 99.8, 101.2, 99.8, 99.2 | 100.1, 100.0, 100.6, 99.7, 100.2 |

TABLE 2-continued

| Preparation | Appearance | Upper portion of the bulk suspension (n = 5) | Middle portion of the bulk suspension (n = 5) | Lower portion of the bulk suspension (n = 5) |
|---|---|---|---|---|
| | | Ciclesonide concentration* (%) (versus theoretical value) | | |
| Comparative Example 4 | white and uniform suspension | 99.8, 100.3, 99.6 98.9, 100.2 | 99.7, 100.5, 99.9 99.8, 101.0 | 99.3, 100.2, 99.0 101.3, 99.8 |
| Comparative Example 5 | white and uniform suspension | 100.8, 101.2, 99.2 99.0, 100.6 | 100.2 99.6, 99.4 100.2 99.7 | 99.5, 99.4, 100.3 100.2, 101.7 |
| Comparative Example 6 | white and uniform suspension | 101.6, 99.0, 99.8 100.3, 100.2 | 99.8, 101.2, 100.0 99.8, 100.4 | 99.8, 102.0, 100.2 99.8, 100.3 |
| Comparative Example 7 | white and uniform suspension | 99.7, 99.9, 99.7 101.6, 100.2 | 100.2, 101.1, 100.8, 100.0, 99.3 | 99.4, 100.2, 99.9 100.3, 99.7 |

*Ratio (percentage) of the ciclesonide concentration calculated from the peak area on high performance liquid chromatography of applied sample to the theoretical ciclesonide concentration**.
**Theoretical ciclesonide concentration means the weight of ciclesonide per the weight of total suspension in manufacturing.

Figure 2:
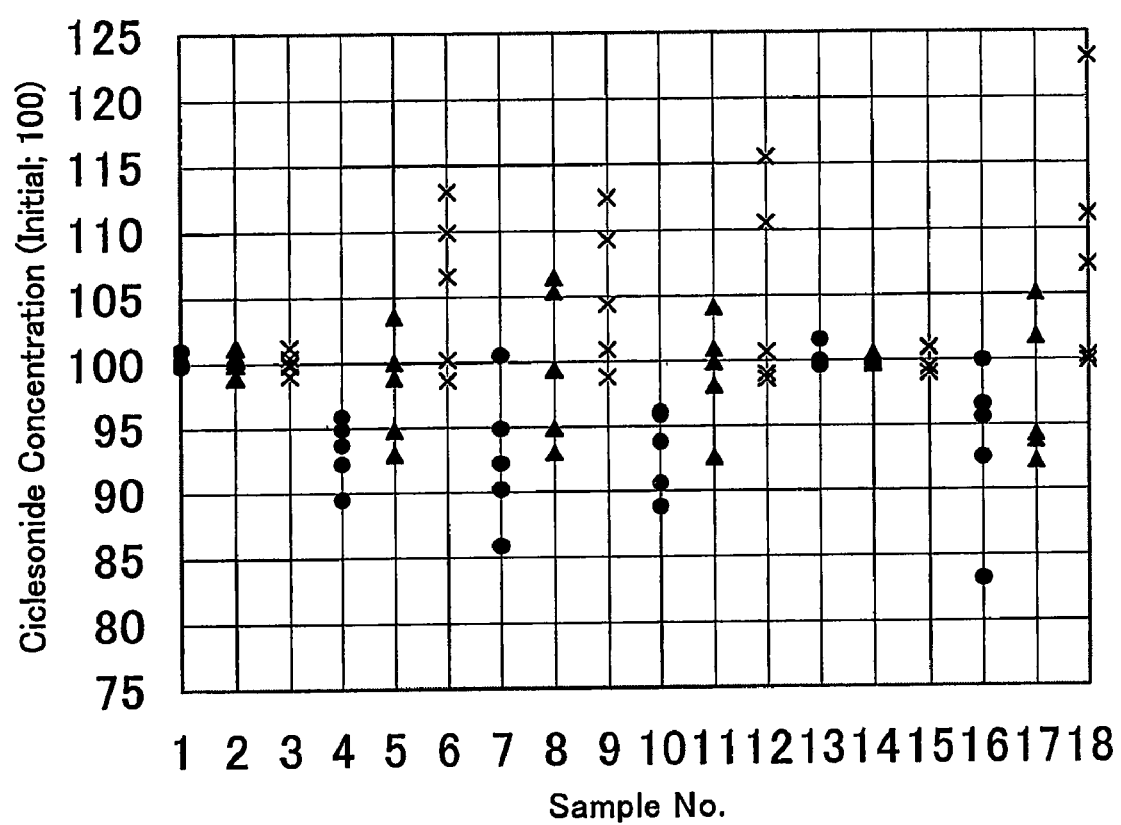
FIG. 2 shows ciclesonide concentration after autoclave, and corresponds to Table 3. Legends in FIG. 2 mean same as those in FIG. 1.

Then as the next step, the suspensions of Example 2 and Comparative Examples 3-7 in 500 mL glass container were sterilized by autoclaving at 121 degrees C. for 20 minutes. Subsequently, the glass container was took out from the equipment for autoclave. After 3-hour-leaveing, the dispersion state of the solid particles in each suspension was observed. Furthermore about 2 g of the suspension were sampled from upper, middle and lower portions of the bulk suspension in the glass container, respectively, followed by the determination of ciclesonide concentration of each portion. Appearances of the ciclesonide aqueous suspension and the uniformity of the ciclesonide concentration after autoclaving are shown in Table 3 and FIG. 2.

TABLE 3

| Preparation | Appearance | Upper portion of the bulk suspension (n = 5) | Middle portion of the bulk suspension (n = 5) | Lower portion of the bulk suspension (n = 5) |
|---|---|---|---|---|
| | | Ciclesonide concentration* (%) (versus theoretical value) | | |
| Example 2 | no change | 100.0, 101.0, 99.9 99.8, 100.1 | 101.2, 98.9, 99.9 100.5, 100.3 | 99.0, 99.8, 101.2 100.4, 100.0 |
| Comparative Example 3 | ditto | 92.2, 94.9, 89.5 95.9, 93.7 | 94.8, 103.5, 98.8 100.0, 92.9 | 109.9, 113.0, 98.6 106.6, 100.2 |
| Comparative Example 4 | ditto | 90.2, 94.9, 92.2 85.9, 100.5 | 99.4, 106.5, 94.9 105.4, 93.0 | 100.9, 112.5, 98.8 109.3, 104.4 |
| Comparative Example 5 | ditto | 93.8, 96.1, 88.8 95.9, 90.6 | 100.9 92.6, 98.1 104.1 99.9 | 110.5, 99.0, 98.6 115.5, 100.7 |
| Comparative Example 6 | large solid appeared | 101.6, 100.0, 99.6 99.8, 100.0 | 100.2, 99.9, 99.7 100.5, 100.3 | 99.5, 99.0, 101.0 99.4, 100.9 |
| Comparative Example 7 | no change | 92.5, 96.6, 100.0 95.6, 83.2 | 94.3, 105.1, 93.8 101.8, 92.2 | 111.1, 123.1, 99.9 107.3, 100.3 |

*Same as Table 2.

The invention claimed is:
1. An autoclaved sterile aqueous suspension comprising ciclesonide and hydroxypropylmethylcellulose, wherein the concentration of the ciclesonide taken from a sample of said suspension after said suspension has been; and it is autoclaved is 95% or more compared to that before the suspension it is autoclaved irrespective of whether the sample is taken from the upper, middle or lower portion of the suspension in bulk.

* * * * *

UNITED STATES PATENT AND TRADEMARK OFFICE
CERTIFICATE OF CORRECTION

| | | |
|---|---|---|
| PATENT NO. | : 8,182,824 B2 | Page 1 of 1 |
| APPLICATION NO. | : 10/519484 | |
| DATED | : May 22, 2012 | |
| INVENTOR(S) | : Yoshihisa Nishibe et al. | |

It is certified that error appears in the above-identified patent and that said Letters Patent is hereby corrected as shown below:

Claim 1, Col. 8, Line 31: Delete "; and it is";
Claim 1, Col. 8, Line 33: Delete "it".

Signed and Sealed this
Fourteenth Day of August, 2012

David J. Kappos
*Director of the United States Patent and Trademark Office*